Figure 1:
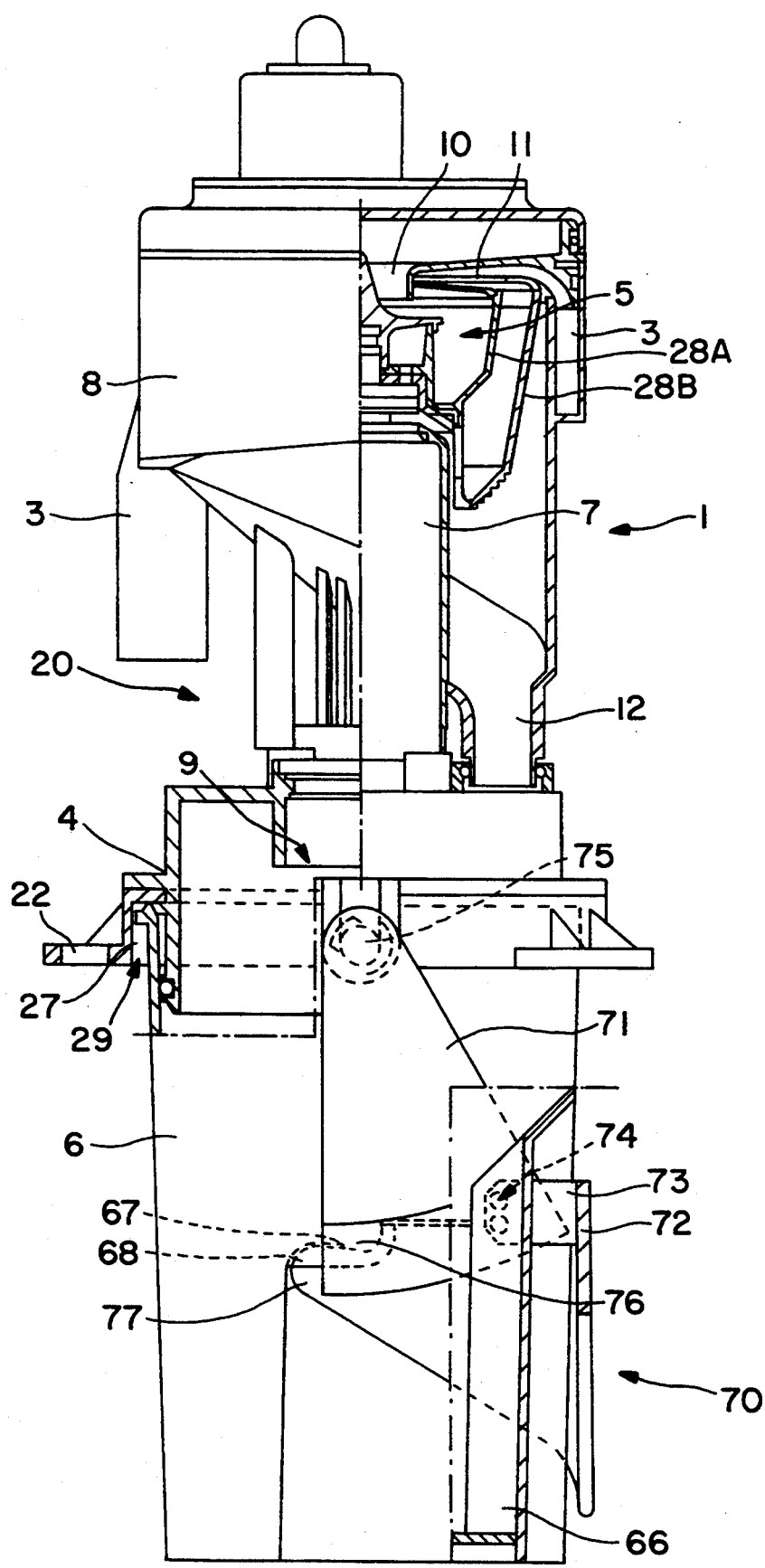

United States Patent [19]

Trawöger et al.

[11] Patent Number: 5,421,996

[45] Date of Patent: Jun. 6, 1995

[54] SEPARATOR FOR SEPARATING WITH LOCKING ELEMENT MOUNTED SENSOR

[76] Inventors: Werner Trawöger, Huebe 26; Bruno Pregenzer, Huebe 30, both of A-6173 Oberperfuss, Austria

[21] Appl. No.: 129,205

[22] PCT Filed: Apr. 1, 1992

[86] PCT No.: PCT/AT92/00042
§ 371 Date: Oct. 8, 1993
§ 102(e) Date: Oct. 8, 1993

[87] PCT Pub. No.: WO92/18061
PCT Pub. Date: Oct. 29, 1992

[30] Foreign Application Priority Data

Apr. 12, 1991 [AT] Austria .................................. 776/91

[51] Int. Cl.[6] .................................................. B01D 21/32
[52] U.S. Cl. .................................. 210/86; 4/263; 210/94; 210/232; 210/261; 433/92; 73/866.5
[58] Field of Search .................. 210/85, 86, 94, 232, 210/261, 262, 294, 360.1, 513; 433/92–97; 4/263; 96/156, 157; 73/866.5

[56] References Cited

U.S. PATENT DOCUMENTS

| 3,078,579 | 2/1963 | Jones et al. | 433/92 |
| 4,564,374 | 1/1986 | Hofmann | 433/92 |
| 5,018,971 | 5/1991 | Trawoger et al. | 433/92 |

FOREIGN PATENT DOCUMENTS

| 0300439 | 7/1988 | European Pat. Off. | 433/92 |
| 8603669 | 7/1986 | WIPO | 433/92 |
| 8904152 | 5/1989 | WIPO | 433/92 |
| 8904641 | 6/1989 | WIPO | 433/92 |

OTHER PUBLICATIONS

"Technische Daten Einbauanleitung Betriebsanleitung Wartungsanleitung, Multi-System TYP 1", Institut fur Bautechnik, Berlin, Nov. 28, 1989.

*Primary Examiner*—Joseph W. Drodge
*Attorney, Agent, or Firm*—Lorusso & Loud

[57] ABSTRACT

A separator for separating a solid and liquid is disclosed which includes a sensor system for detecting the level of solid that is separated from the liquid and accumulated in a settling tank. A movable locking element locks the separator to the settling tank, and is movable between an open and a closed position. The sensor system is attached to the movable locking element thereby providing protection for the sensing elements which include at least one light barrier.

4 Claims, 3 Drawing Sheets

SEPARATOR FOR SEPARATING WITH LOCKING ELEMENT MOUNTED SENSOR

The present invention relates to a separator for separating a solid-liquid mixture, in particular the waste water originating from dental practice, with an inlet for the mixture that is to be separated, with an outlet for the liquid that has been separated off, and with a removable settling container for the solids, with at least one moveable locking element that, when in the open position permits removal of the settling container and in the closed position locks the settling container to the separator, and with a sensing system to identify at least one pre-set level of its contents. In addition, it is preferred that the separator incorporate a settling tank that has light-permeable walls and a sensing system that incorporates at least one light barrier.

A separator of this kind is described, for example, in the technical handbook for the "Metasys Multi-system Type 1" amalgam separator (May 1990) by Metasys Produktionsegellschaft m.b.H. & Co. KG, Innsbruck. This separator incorporates a mounting for the settling tank on which a printed circuit is mounted, this printed circuit extending parallel to the settling tank. The sensor system extends from this, and when the settling tank is installed, this identifies first the 95% level and then the maximum level. Snap fasteners which overcome a dead point are provided to fix the settling tank to the separator. The installation of the sensing system on the circuit board requires a relatively unprotected arrangement and it is the task of the present invention to create a separator in which this disadvantage has been eliminated. According to the present invention, this has been achieved in that the sensor system is arranged on the moveable locking element.

Because of the arrangement of the sensor system on the locking element, this is spatially separated from the circuit board so that it can be better protected when installed. There is no longer any requirement for a dedicated mounting for the sensor system because the locking element must at least partially overlap the settling tank. Because of the fact that it has to be fitted to the side of the locking element that faces the settling tank, the sensor system is covered by this to the outside and is similarly protected by this.

In a preferred embodiment in which the settling tank incorporates a light-permeable wall and at least one light barrier as a sensing device, provision is made such that the locking element is configured as a pivoting bale that has pivoting arms that are hinged onto it on both sides of the settling tank and in that the sensor elements of each light barrier is arranged on the parts of the pivoting bale that extend perpendicular to the pivot axis.

Because of the fact that, in order to provide for the most trouble-free identification of the level in the settling tank, it is more favourable to monitor a part area of the settling tank, it is preferred that this be provided with a rib that projects from a side wall and which can be overlapped by the sensing system. Then, according to the present invention, the pivoting bale incorporates a cross-piece that joins the pivot arms and from which tabs extend parallel to the pivot arms, said arms, in the closed position, extending on both sides of the rib on which the sensor elements are arranged.

In particular, in this case, additional sensor elements can be provided on the pivoting bale to identify the liquid levels in the settling tank at which a pump that removes the liquid is started and stopped.

The present invention will be described in greater detal below on the basis of the drawings appended hereto and without being restricted to these.

Figure 2:
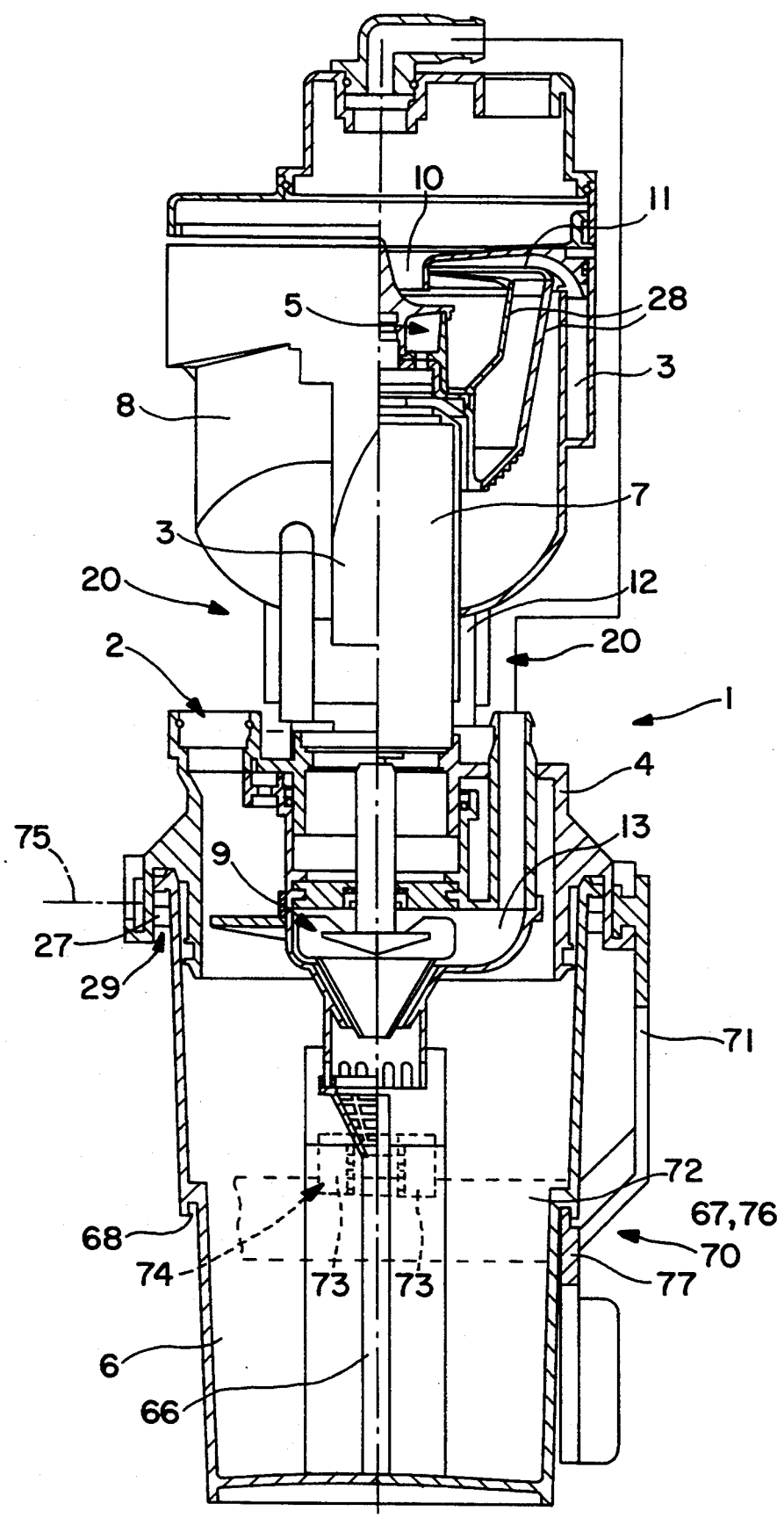
Figure 3:
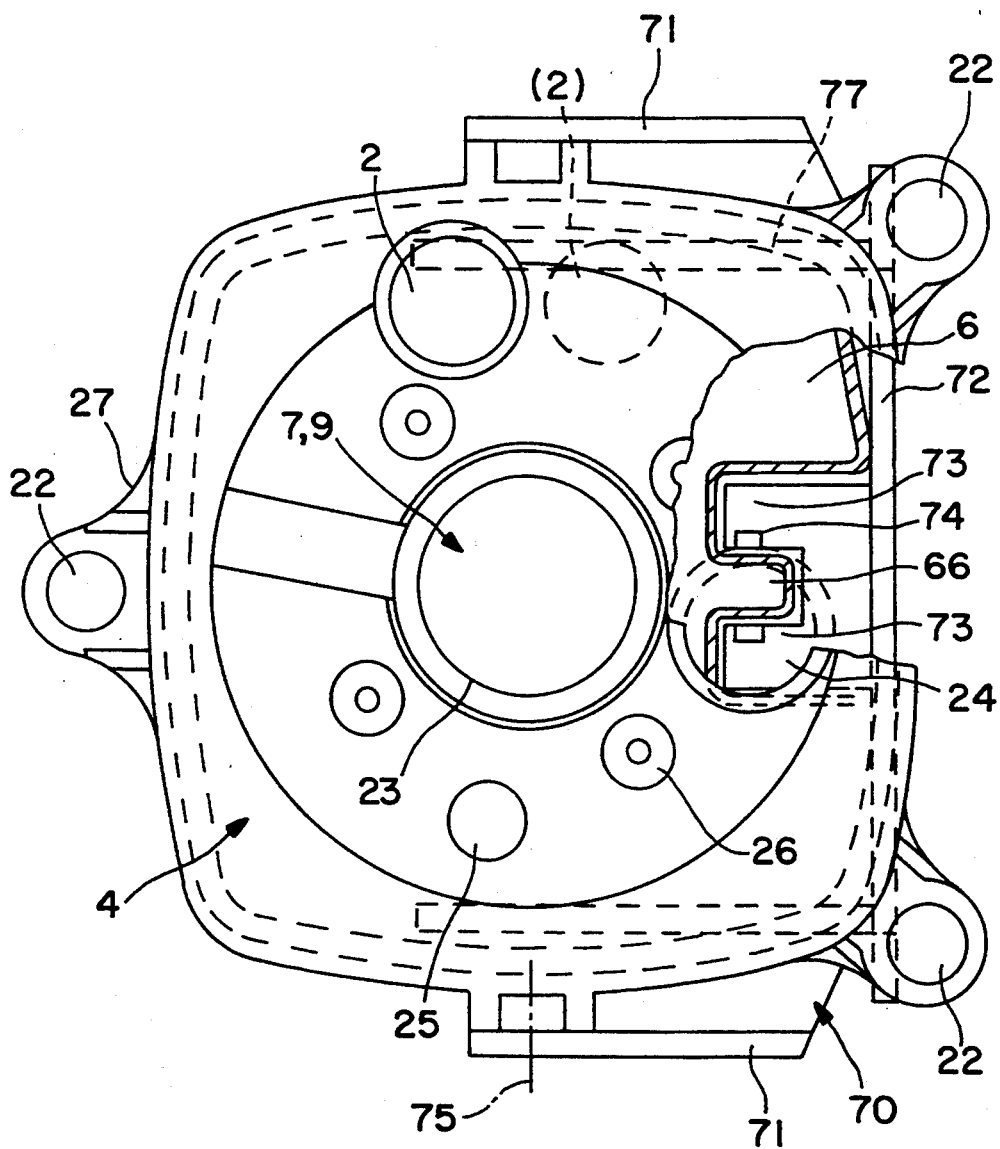

FIGS. 1 and 2 show vertical cross-sections through a separator according to the present invention; and FIG. 3 shows a plan view of the installation housing of the separator.

The separator 1 comprises a settling 6 tank that is used to sediment the solids, and a full-casing centrifuge 5 that is incorporated in the through-flow direction, on the settling tank 60. Both are arranged on an installation housing 4 that can be mounted on a dental chair or the like, so that the settling tank 6 is mounted so as to be removable from the installation housing 4 from below, as can be seen in greater detal in FIGS. 1 and 2. The installation housing 4 is provided with attachment drillings 22 that are provided, in particular, on a dedicated adaptor 27. Appropriate adaptors 27 are available for particular installations and the installation housing 4 can be provided with these. There are other transit-type openings 7 in the installation housing 4: there is an opening 23 used to accommodate the motor 7 for the centrifuge 5 and for a pump 9, an opening 24 for insertion of the solids drain 12 of the centrifuge 5, an opening 25 for routing a connection line 19, which is only shown diagrammatically, between the pump line and the centrifuge 5, the drillings 26 for mounting bolts for the joint attachment of the centrifuge housing 8 and of the pump housing 13, and the mixture inlet 2 through which the mixture coming from the air separator device and/or a rinsing basin can be introduced into the separator 1. As is shown, a second mixture inlet (2) can be provided so that each feedline can be attached to its own dedicated mixture inlet 2 (2). The centrifuge housing 8, which is fixed to the installation housing 4, is tapered in its lower part, the motor 7 being arranged centrally, and in addition it also contains the two centrifuge containers 20 of the full casing centrifuge 5, these being arranged one inside the other. An inlet 10 for the mixture that is pumped up through the connecting line 19 from the settling tank 6 opens out into the inner centrifuge container 28A, and the outer centrifuge container 28B has a transfer opening 11 through which the clarified liquid moves into the liquid outlet 3. When the centrifuge 5 is stationary, solids flow downwards under gravity and pass through the eccentrically arranged solid drain 12, through the opening 24, into the settling tank 6. An angular connector (not shown herein) is inserted into the mixture inlet 2 (2) of the installation housing 4 so as to be rotatable. Both the mixture inlet 2 (2) and the opening 25 for the connector line 19 are located in the space 20 that results from the taper of the centrifuge housing 8, which is to say within the space required for the centrifuge 5, and this results in an extremely compact and space-saving embodiment.

A groove 29 in the installation housing 4 that is open underneath serves as a slide for the settling tank 6. This is fixed in place by means of a stirrup-shaped locking element 70 that is mounted so as to be able to pivot about a shaft 75 on the outside wall of the groove 29. The locking element 70 has two pivoting arms 71 that extend at the sides outside the settling tank 6 and a cross-piece 72 that joins these. A bar 77 that is parallel to these is associated with each pivot arm 71 and this fits in a pocket 68 in the settling tank 6 when in the closed position. A detent recess 76 that is provided in at least one bar 77 centers into detent on a cam 67 in the pocket 68 of the settling tank 6. The settling tank 6 is made from transparent plastic and has longitudinal rib 66 that projects on a wall that faces the cross-piece 72. The cross-piece 72 has projecting tabs 73 that are parallel to the side walls of the longitudinal rib 66, on which a sensing device 74 is formed. This includes at least one or, in the embodiment shown, two light barriers such that each beam of light passes through the longitudinal rib 66 and permits measurement of the level of the sedimented solids. The lower light barrier responds when the level to which the container is full reaches 95% of the maximum and emits a warning signal, whereas when the second upper light barrier that indicates the maximum filling level responds, the separator, preferably the whole of the suction system, is shut down. In order to replace the settling tank, the locking element 78 is swung upwards so that the bars 77 release the settling tank 6, which can then be removed downwards. The sensor system 74 could also comprise additional sensor elements to detect the two levels of liquid that collect above the solids at which the motor 7 would be switched on and off.

We claim:

1. A separator for separating a mixture of solids and liquids, said separator comprising a housing having an inlet for the mixture that is to be separated and an outlet for discharging separated liquids, a settling tank arranged for collecting separated solids and removably arranged on the housing, at least one locking element overlapping at least partially the settling tank, said locking element being movable between an open position permitting removal of the settling tank and a closed position in which the settling tank is locked to the housing, a sensor system operable, for identifying at least one pre-set level of solids in the settling tank, said sensor system being arranged on the locking element and being movable with the locking element between said open position and said closed position.

2. A separator as claimed in claim 1, wherein said locking element comprises two pivot arms hinged to said housing and a cross-piece connecting said pivot arms.

3. A separator as claimed in claim 1, wherein said settling tank has a light-permeable wall, and said sensor system has at least one light barrier penetrating the light-permeable wall in said closed position of said at least one locking element.

4. A separator as claimed in claim 3, wherein said light-permeable wall comprises a longitudinal rib which has two parallel sides, and wherein said at least one locking element each comprises two tabs extending parallel to said parallel sides of the rib, said at least one light barrier each having a sensor element arranged on each of said tabs, and said rib lying between said tabs in said closed position of said at least one locking element.

* * * * *